United States Patent [19]
Keller

[11] Patent Number: 5,456,719
[45] Date of Patent: Oct. 10, 1995

[54] ENDOPROSTHESIS WITH A PROSTHESIS PART MADE OF VISCOELASTIC SYNTHETIC RESIN

[75] Inventor: Arnold Keller, Kayhude, Germany

[73] Assignee: Waldemar Link GmbH & Co, Hamburg, Germany

[21] Appl. No.: 211,092

[22] PCT Filed: Sep. 18, 1992

[86] PCT No.: PCT/EP92/02163
§ 371 Date: Mar. 18, 1994
§ 102(e) Date: Mar. 18, 1994

[87] PCT Pub. No.: WO93/05728
PCT Pub. Date: Apr. 1, 1993

[30] Foreign Application Priority Data
Sep. 19, 1991 [DE] Germany .................. 9111729 U

[51] Int. Cl.⁶ ........................................... A61F 2/02
[52] U.S. Cl. ....................... 623/11; 606/70; 606/71
[58] Field of Search .................... 606/69, 70, 71, 606/72, 73, 76; 411/166, 174, 175, 176, 185, 187, 188; 623/11

[56] References Cited
U.S. PATENT DOCUMENTS 1,368,896  2/1921  Chambley .................. 411/166
1,813,053  7/1931  Hosking .................... 411/166
3,825,051  7/1974  Sigmund .................... 411/188
4,822,366  4/1989  Bolesky ..................... 623/20

FOREIGN PATENT DOCUMENTS 0290967  11/1988  European Pat. Off. .
2402099   4/1979  France ..................... 411/176
2252828   5/1973  Germany .
91/01691  2/1991  WIPO .

Primary Examiner—Tamara L. Graysay
Attorney, Agent, or Firm—Chilton, Alix & Van Kirk

[57] ABSTRACT

Endoprosthesis with a prosthesis part (4) of viscoelastic synthetic resin such as polyethylene which is intended to be fastened to a support part (1) of more resistant material such as metal by a screw element (3). The screw element has a release locking which consists of a sequence of elevations (14) and depressions which dig into a surface (13) of the synthetic resin with plastic deformation of the latter. For this purpose, a pair of surfaces on the screw element and the synthetic resin part are chosen, whose spacing is determined by the design (in particular by hard stops 8, 9) and which surfaces do not transmit the force with which the screw element is tightened.

4 Claims, 2 Drawing Sheets

ENDOPROSTHESIS WITH A PROSTHESIS PART MADE OF VISCOELASTIC SYNTHETIC RESIN

With endoprostheses, a part made of viscoelastic synthetic resin such as polyethylene, which forms, for example, a joint surface of the endoprosthesis, often has to be fixed to a metal support part. This screw requires locking against undesired rotation in the release direction. In mechanical engineering, a screw lock is known (EP-A-0290967) which is based on the fact that the force-transmitting end face of the screw is provided with radial ribs which dig into the countersurface. The depth to which the ribs penetrate into the countersurface is determined by the force with which the screw is tightened. It can be limited by providing deepened contact surfaces between the ribs, which contact surfaces, at the intended penetration depth of the ribs, bear against the countersurface. However, the particular penetration depth of the ribs is dependent on the screwing force. If the screw is loose, the locking also no longer functions. In the case underlying the invention, on the other hand, only a slight screwing force, if any, normally acts on the synthetic resin part to be fastened; the known principle can therefore not be directly used here.

The invention therefore aims to find a screw lock which is adapted to these specific conditions. The solution according to the invention is provided by an assembly comprising a prosthesis part of viscoelastic synthetic resin fastened to a support part of the endoprosthesis by means of a screw element. The support part is more resistant to plastic displacement than the synthetic resin prosthesis part and is provided with an abutment while the screw element includes a head and a shank with a stop surface on the shank in spaced relationship to the head. The stop surface cooperates with the abutment to limit axial movement of the head relative to the prosthesis part and to seat the screw element. The seated position of the screw element is determined by means of the interacting stop surface on the screw element and the abutment on the support part. The head of the screw element has saw-toothed elevations facing the synthetic resin prosthesis part. The saw-toothed elevations are formed by tapered flanks forming leading surfaces during tightening of the screw element and steeper tooth flanks directed against the release direction of the screw element. In this way, the leading surfaces effect a viscoelastic displacement of the synthetic resin during tightening of the screw element, after which the displaced synthetic resin volume relaxes at least partly into the depressions formed between the elevations so that the steeper tooth flanks engage the relaxed surface of the synthetic resin prosthesis to resist loosening of the screw element.

By virtue of the fact that the relative position of the locking surface of the screw element on the one hand and of the surface of the synthetic resin part interacting therewith is determined by the design, the locking action is independent of the screwing force. It is also ensured that the synthetic resin part cannot be damaged by the fact that the locking surface is tightened with too great an assembly force. Rather, it is ensured under all assembly conditions that the synthetic resin material can only be plastically stressed to a predetermined degree.

The elevations and depressions are designed such that only a plastic material displacement of the synthetic resin occurs, which is subsequently at least partly eliminated again by relaxation. The relaxation provides a mutual interlocking of the locking surface with the associated synthetic resin surface, and thus the desired mutual locking action between the screw element and synthetic resin. The elevations or depressions of the screw element are preferably designed so as to be saw-toothed in the circumferential direction, their steeper tooth flanks being directed against the release direction.

If a screw is used for fastening, it may have a thread at its end, which interacts with a threaded bore in the metal support part, and may also have, adjacent to said thread at the head end, a thickened shank which forms a stop on the metal support part, so that, when the screw is in the end position, the head is located at a predetermined distance from the surface of the metal support part, which distance corresponds to the thickness of the polyethylene part. In this case, most of the screwing force interacts with the support part and only a small proportion with the polyethylene part. By this means, the position of the locking surface is determined by the design. This screw shape is known per se (U.S. Pat. No. 4,822,366), but not in the context of screw locking.

In another embodiment of the invention, the locking surface is predetermined by the design by the fact that it is arranged on a circumferential surface and interacts with a correspondingly undersized bore in the synthetic resin part.

The invention is explained in greater detail below with reference to the drawing which illustrates the exemplary embodiments and in which.

Figure 1:
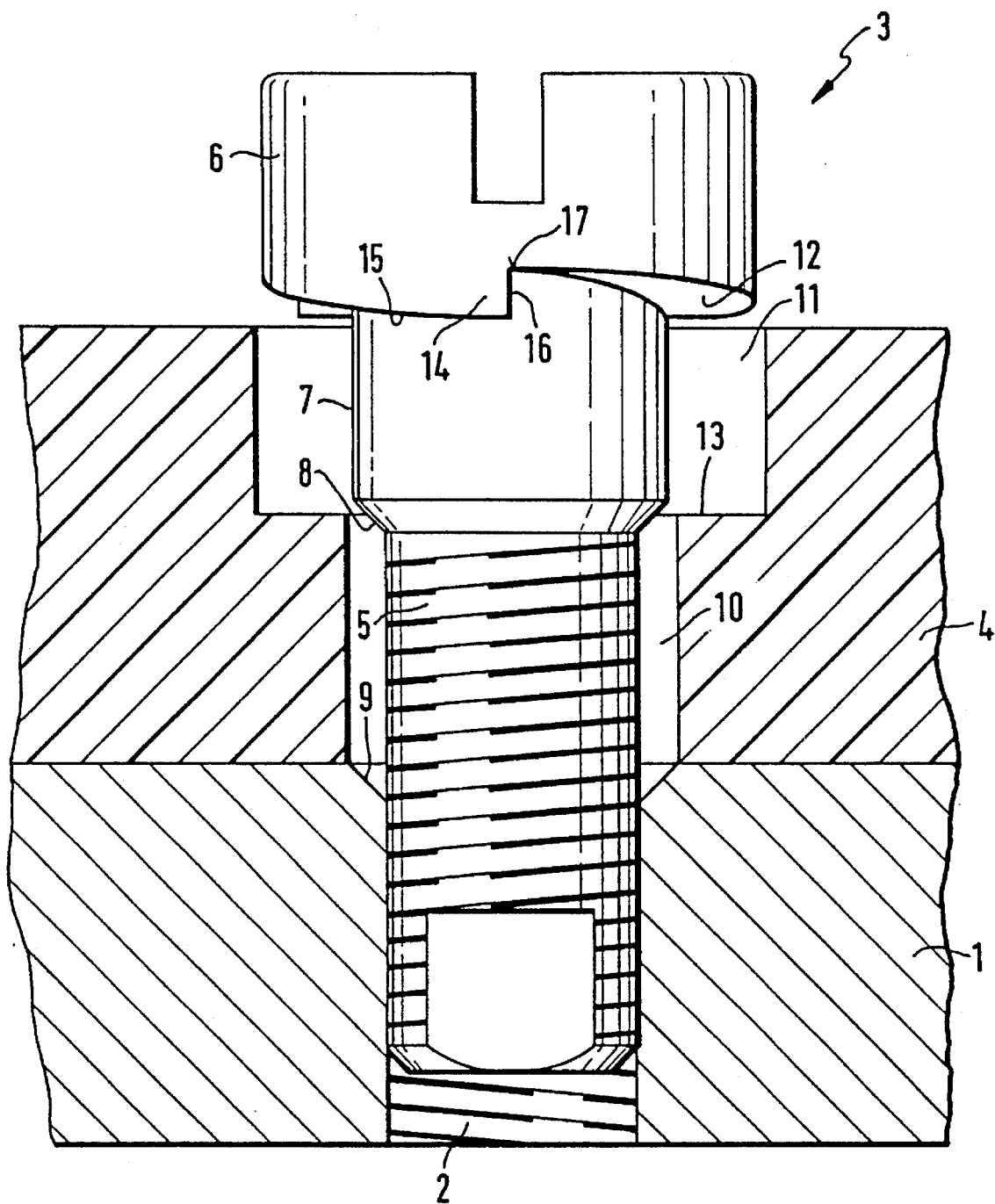
FIG. 1 shows a longitudinal section through a first embodiment.

The polyethylene part 4 is intended to be fastened on the metal support part 1 with threaded bore 2 by means of the screw 3. Since the force usually occurring during tightening of the screw is greater than the force which is expected of the polyethylene, a shank 7 of greater diameter is arranged between the thread 5 and the head 6 of the screw, which shank forms a stop surface 8 which interacts with a stop surface 9 on the support part 1 when the screw has reached the intended end position.

To receive the screw, the polyethylene part 4 has a bore 10 which is enlarged to receive the screw head 6 at 11. The bottom surface 12 of the screw head therefore interacts with the bearing surface 13 of the polyethylene part. Normally, the distance between the bottom surface 12 and the stop surface 8 of the screw would be made approximately exactly the same size as the distance between the bearing surface 13 of the polyethylene part and the stop surface 9 of the support part. If the stop surfaces 8 and 9 bear against one another under tension to determine the end position of the screw, the bottom surface 12 of the screw head 6 would then lie directly on the bearing surface 13 of the polyethylene part.

In the embodiment according to FIG. 1, however, the bottom surface 12 of the screw head, as locking surface, is provided with saw teeth 14 which extend in the circumferential direction and on the one hand are delimited by the shallow flanks 15 and on the other hand by the steep flanks 16, these surfaces being located such that the shallow flanks 15 lead during tightening of the screw and the steep flanks 16 lead during release of the screw. Furthermore, the distance between the tips of the teeth 14 and the stop surface 8 is less than the distance between the bearing surface 13 and the stop surface 9, so that, during tightening of the screw, the saw teeth 14 dig into the compliant polyethylene material of the bearing surface 13, material being at least partly plastically displaced out of the way of the saw teeth 14. This has the consequence that, directly after the tightening, only a little synthetic resin material, if any, which might prevent the release of the screw, is disposed opposite the steep flanks 16. However, since polyethylene and many other synthetic resins, which are therefore also suitable for the subject of the invention, are viscoelastic and therefore manifest relaxation, that is to say the property, after a deformation, to slowly deform back to a shape which approaches the original shape, synthetic resin gradually penetrates back into the empty spaces between adjacent saw teeth 14 and thus also, at least partly, fills the space in front of the steep flanks 16. The screw can therefore not be released without this synthetic resin material being removed, which, because of the steepness of these flanks, is possible only with considerable force application. This force application is all the greater, since the deformation because of the flank steepness cannot take place by simple plastic displacement, but rather requires destruction of the synthetic resin material. This is fully adequate to provide release locking with respect to the small forces which are to be expected in the applications described.

The height difference between the stop surface 9 of the support part i and the bearing surface 13 of the polyethylene part may be exactly as large as the height difference between the stop surface 8 of the screw and the tooth base 17 of the saw teeth, so that the complete saw-tooth volume is available for the displacement of the synthetic resin. However, the height difference between the surfaces 9 and 13 may also be somewhat lower, namely may correspond approximately to the average distance between the stop surface 8 and the shallow flank 15 of the saw teeth. In such a case, the material volume displaced by the advancing half of the saw teeth corresponds approximately to that volume which is available in the upper half of the tooth gaps to receive the displaced synthetic resin material. The optimum dimensioning may be easily determined by experimentation.

Figure 2:
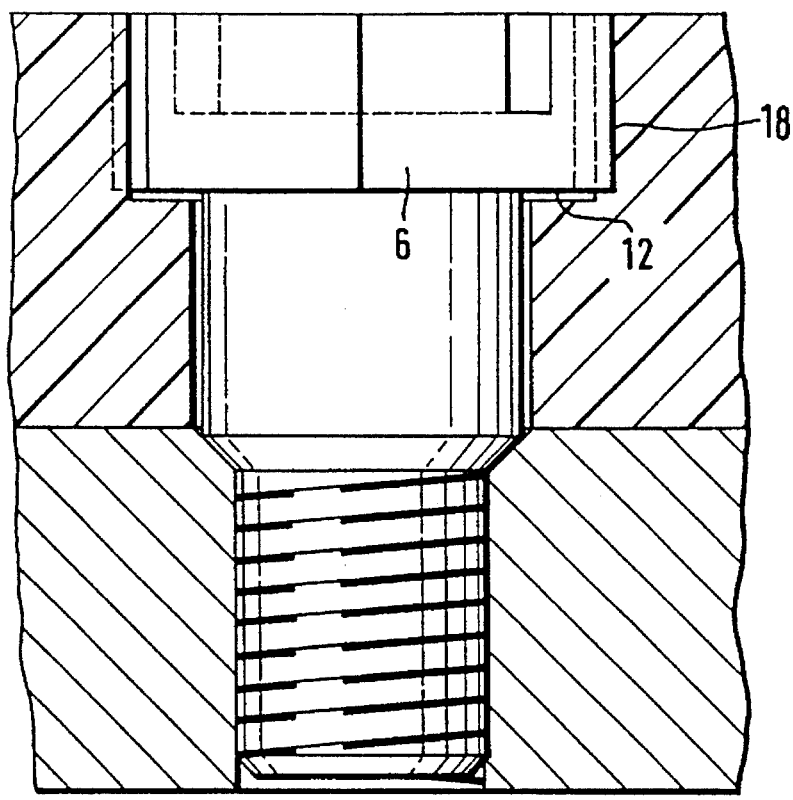
FIG. 2 shows a longitudinal section through a second embodiment.
Figure 3:
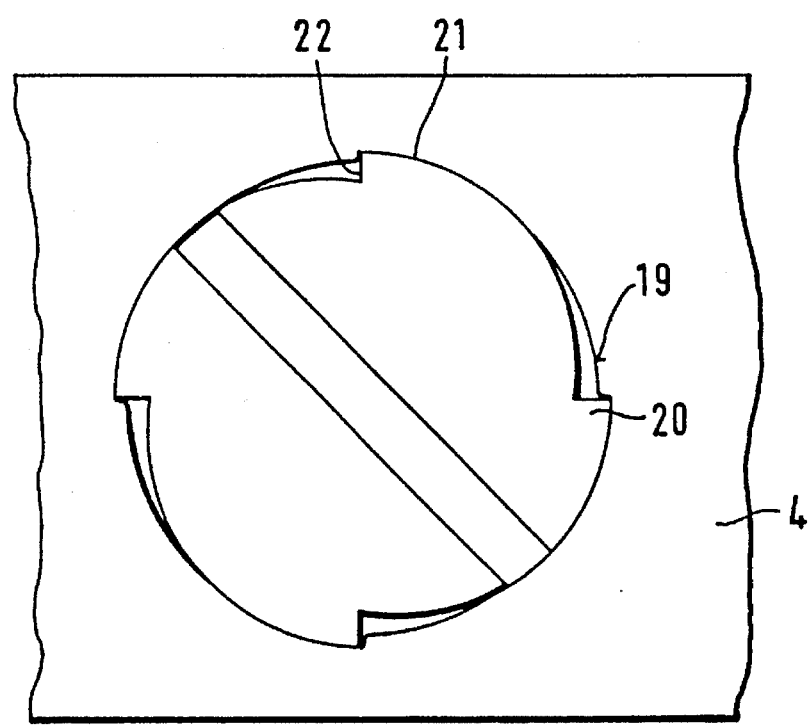
FIG. 3 shows a plan view of the second embodiment.

The arrangement according to FIGS. 2 and 3, unless otherwise described below, is the same as that according to FIG. 1. The difference consists in the fact that, not the bottom surface 12 of the screw head 6 is used for forming the locking surface, but its circumferential surface 18 which interacts with the surface 19 of the bore, surrounding the screw head 6, in the synthetic resin part 4. The circumferential surface 18 is provided with saw-tooth elevations 20, whose foremost flank 21, in the screw-in direction, rises gently to permit plastic displacement of the surrounding material, whereas the reverse side 22 falls away steeply to resist rotation in the release direction and to destroy the synthetic resin material. In the representation according to FIG. 3, it can be seen that, after the plastic displacement during the screwing-in of the screw 3, the surface 19 of the synthetic resin material has flowed back into the depressions formed between the saw teeth 20 and thereby interacts positively with the rear flanks 22 of the saw teeth.

For the purposes according to the invention, a saw-tooth form is particularly advantageous. However, it is also suitable to use projections on the bottom surface of the screw elements which require no greater force threshold during the release movement than during the tightening of the screw, since even relatively low deformation forces are very often adequate for locking the screw.

The term screw element includes screws, nuts and, furthermore, all elements which can be brought into contact with a bearing surface by a screwing movement.

An advantageous secondary effect of the invention consists in the fact that, by virtue of the destruction of the synthetic resin during release of the screw, it is reliably possible to prevent impermissible reuse of a synthetic resin prosthesis part.

I claim:

1. An endoprosthesis comprising a prosthesis part of viscoelastic synthetic resin fastened to a support part by a screw element, the material of the support part being more resistant to plastic displacement than the synthetic resin prosthesis part, characterized in that the support part is provided with an abutment and the screw element (3) has a head and a shank with a stop surface on the shank in spaced relationship to said head, said stop surface cooperating with said abutment to limit axial movement of said head relative to said prosthesis part and seat the screw element on the support part, said head having saw-toothed elevations (14) facing the synthetic resin prosthesis part fastened thereby, said saw-toothed elevations (14) having tapered flanks forming leading surfaces during tightening of the screw element and steeper tooth flanks (16) which are directed against the release direction of the screw element whereby the leading surfaces effect a viscoelastic displacement of the synthetic resin prosthesis part during tightening of the screw element after which the displaced synthetic resin volume relaxes at least partly into the depressions formed between the elevations whereby the steeper tooth flanks engage the relaxed synthetic resin prosthesis, the seated position of the screw element being determined by the interacting stop surface (8) on the screw element and the abutment (9) on the support part (1).

2. An endoprosthesis comprising a prosthesis part of viscoelastic synthetic resin fastened to a support part by a screw element, the material of the support part being more resistant to plastic displacement than the synthetic resin prosthesis part, characterized in that the prosthesis part includes a bore having a defining surface, the support part being provided with an abutment and the screw element (3) having a head and a shank with a stop surface on the shank in spaced relationship to said head, said stop surface cooperating with said abutment to limit axial movement of said head relative to said prosthesis part, said head having a circumferential surface (18) with saw-toothed elevations (20) engaging the bore defining surface of the prosthetic part, said elevations being provided with tapered flanks (21) forming leading surfaces during tightening of the screw element and steeper tooth flanks (22) which are directed against the release direction of the screw element whereby the leading surfaces effect a viscoelastic displacement of the synthetic resin after which the displaced synthetic resin volume relaxes at least partly into the depressions formed between the elevations, the bore defining surface (19) having an original position between the position of the elevations (20) and the position of the depressions of the circumferential surface (18).

3. The endoprosthesis of claim 1 wherein the viscoelastic synthetic resin is polyethylene.

4. The endoprosthesis of claim 2 wherein the viscoelastic synthetic resin is polyethylene.

* * * * *